US012569446B2

(12) United States Patent
Xiang et al.

(10) Patent No.: US 12,569,446 B2
(45) Date of Patent: \*Mar. 10, 2026

(54) ENTERAL SUSTAINED-RELEASE SUGAR ALCOHOL ADDITIVE AND PREPARATION METHOD AND APPLICATION THEREOF

(71) Applicant: ZHEJIANG HUAKANG PHARMACEUTICAL CO., LTD., Quzhou (CN)

(72) Inventors: Shasha Xiang, Quzhou (CN); Xuan Zhu, Quzhou (CN); Lihua Shi, Quzhou (CN); Kun Ye, Quzhou (CN); Mian Li, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/228,731

(22) Filed: Jun. 4, 2025

(65) Prior Publication Data

US 2025/0295594 A1 Sep. 25, 2025

Related U.S. Application Data

(63) Continuation-in-part of application No. 17/775,193, filed as application No. PCT/CN2021/075696 on Feb. 7, 2021.

(30) Foreign Application Priority Data

Feb. 11, 2020 (CN) .......................... 202010087312.6

(51) Int. Cl.
| | |
|---|---|
| *A61K 9/22* | (2006.01) |
| *A61K 9/20* | (2006.01) |
| *A61K 9/28* | (2006.01) |
| *A61K 9/34* | (2006.01) |
| *A61K 35/741* | (2015.01) |
| *A61K 35/745* | (2015.01) |
| *A61K 35/747* | (2015.01) |
| *A61K 35/00* | (2006.01) |

(52) U.S. Cl.
CPC .......... *A61K 9/2086* (2013.01); *A61K 9/2018* (2013.01); *A61K 9/205* (2013.01); *A61K 9/2893* (2013.01); *A61K 35/741* (2013.01); *A61K 35/745* (2013.01); *A61K 35/747* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 9,610,307 B2 | 4/2017 | Berry et al. | |
| 10,548,844 B2 | 2/2020 | Anselmo et al. | |
| 2008/0305150 A1* | 12/2008 | Chen ....................... | A61J 3/005 |
| | | | 514/781 |
| 2016/0361320 A1 | 12/2016 | Zhao et al. | |
| 2018/0296582 A1* | 10/2018 | von Maltzahn ...... | A61K 31/047 |

FOREIGN PATENT DOCUMENTS

| | | |
|---|---|---|
| CN | 105595359 A | 5/2016 |
| CN | 107259577 A | 10/2017 |
| CN | 107530381 A | 1/2018 |
| CN | 109364096 A | 2/2019 |
| CN | 109528683 A | 3/2019 |
| CN | 110584119 A | 12/2019 |

OTHER PUBLICATIONS

Decision to Grant a Patent in Chinese Application No. 202010087312.6 mailed on Aug. 29, 2022, 6 pages.

* cited by examiner

*Primary Examiner* — Michelle F. Paguio Frising
(74) *Attorney, Agent, or Firm* — METIS IP LLC

(57) ABSTRACT

An enteral sustained-release sugar alcohol additive including an inner layer structure and an outer layer structure is provided. The inner layer structure contains components of xylitol and agar, and the outer layer structure contains components of carrageenan or gellan gum or xanthan gum or guar gum, vitamin B12, L-arabinose, and fermented *Bifidobacterium* or fermented *Propionibacterium* or fermented *Lactobacillus*. A method of preparing an enteral sustained-release sugar alcohol additive and an application thereof are further provided.

4 Claims, 3 Drawing Sheets

ENTERAL SUSTAINED-RELEASE SUGAR ALCOHOL ADDITIVE AND PREPARATION METHOD AND APPLICATION THEREOF

CROSS-REFERENCE TO RELATED APPLICATIONS

This application is a continuation-in-part of U.S. application Ser. No. 17/775,193, filed on May 6, 2022, which is a 371 of International Application No. PCT/CN2021/075696, filed on Feb. 7, 2021, which claims priority to Chinese Application No. 202010087312.6, filed on Feb. 11, 2020, the entire contents of each of which are incorporated herein by reference.

TECHNICAL FIELD

The present disclosure relates to the field of preparation technologies of enteral sustained-release products, in particular to an enteral sustained-release sugar alcohol additive and a preparation method and an application thereof.

BACKGROUND

After being absorbed, propionate is mainly metabolized in liver to participate in gluconeogenesis and inhibit synthesis of cholesterol. However, various researches show that propionates ingested exogenously and generated in body have different effects. The exogenous propionate has significant impact on many metabolic processes of the individuals. Propionate is a short-chain fatty acid. Under normal circumstances, microorganisms in a human body are capable of generating propionate by fermenting un-completely digested carbohydrate in colon and the propionate is beneficial to the human body. But, the exogenous propionate may lead to hyperglycemia and a high level of insulin in a short period, and may even lead to more severe symptoms such as obesity and insulin resistance or the like after a long period of ingestion.

Fructo-oligosaccharide and polysaccharide have the function of generating propionate in intestinal tract. But, neither of fructo-oligosaccharide and polysaccharide can synthesize propionate with a high concentration at a fixed point. The enteral utilization rate of polysaccharide is low and may easily lead to problems of flatulence and the like. Fructo-oligosaccharide may also lead to the problems of excess generation of gas and unstable generation of acid and the like, and even to metabolic disorder of liver and the like due to excess generation of fructose.

SUMMARY

In order to solve the above technical problems, the present disclosure provides an enteral sustained-release sugar alcohol additive and a preparation method and an application thereof so as to promote human body health and eliminate metabolic side effect possibly resulting from propionate, thereby achieving slow release of the enteral sustained-release sugar alcohol additive in intestinal tract and its fixed-point release in colon.

The present disclosure provides an enteral sustained-release sugar alcohol additive. The enteral sustained-release sugar alcohol additive includes an inner layer structure and an outer layer structure, wherein the inner layer structure contains xylitol and agar, and the outer layer structure contains one of carrageenan or gellan gum or xanthan gum or guar gum, vitamin B12, L-arabinose, and fermented *Bifidobacterium* or fermented *Propionibacterium* or fermented *Lactobacillus*.

The present disclosure further provides a method of preparing the enteral sustained-release sugar alcohol additive as described above. The method includes the following steps:

at step 1, mixing and sterilizing xylitol and agar, placing the mixture into a ball mould and standing the mixture for cooling so as to prepare xylitol agar pellets, a concentration of the agar being 2%;

at step 2, preparing a carrageenan solution or gellan gum solution or xanthan gum solution or guar gum solution, adding the vitamin B12 and the L-arabinose to the carrageenan solution or the gellan gum solution or the xanthan gum solution or the guar gum solution and mixing to uniformity so as to obtain a mixed solution, and then wrapping the xylitol agar pellets in step 1 with the mixed solution to obtain xylitol agar two-layer colloidal pellets wrapped with the mixed solution; and at step 3, placing the two-layer colloidal pellets prepared in step 2 into a fermented *Bifidobacterium* medium or a fermented *Propionibacterium* medium or a fermented *Lactobacillus* medium for culturing, and then taking out the pellets for freeze drying or hot air drying to obtain the enteral sustained-release sugar alcohol additive.

In some embodiments, in step 1, a sterilization condition is sterilizing for 15 min at a temperature of 121° C.

In some embodiments, in step 2, a process of preparing the carrageenan solution or the gellan gum solution or the xanthan gum solution or the guar gum solution includes: weighing 2 g of the carrageenan or the gellan gum or the xanthan gum or the guar gum and dissolving in 100 ml of distilled water, sterilizing for 15 min at a temperature of 121° C. and cooling down to a temperature of 50° C.-60° C.

In some embodiments, in step 3, a concentration of *Bifidobacterium* or *Propionibacterium* or *Lactobacillus*, in the fermented *Bifidobacterium* medium or the fermented *Propionibacterium* medium or the fermented *Lactobacillus* medium is $10^9$ CFU/mL; the two-layer colloidal pellets are placed in the fermented *Bifidobacterium* medium or the fermented *Propionibacterium* medium or the fermented *Lactobacillus* medium for culturing for 24 h, wherein a condition of freeze or hot air drying is freeze drying for 1 h-24 h or hot air drying for 30 min.

The present disclosure further provides an application of the enteral sustained-release sugar alcohol additive as described above. The enteral sustained-release sugar alcohol additive is applied to foodstuff.

The present disclosure further provides an application of an enteral sustained-release sugar alcohol additive prepared using the above method of preparing an enteral sustained-release sugar alcohol additive. The enteral sustained-release sugar alcohol additive is applied to foodstuff.

Compared with the prior art, the enteral sustained-release sugar alcohol additive and the preparation method and the application thereof in the present disclosure have the following advantages.

1. With xylitol, L-arabinose and vitamin B12, directional regulation to intestinal microorganisms is achieved and enteral high-concentration synthesis of propionate can be realized.

2. With double layer embedding technology, enteral sustained release and layer-by-layer release of sugar alcohol can be achieved.

3. With the pellet technology of the method, stability of *Bifidobacterium* or *Propionibacterium* or *Lactobacillus* products is achieved.

DETAILED DESCRIPTION OF THE EMBODIMENTS

Figure 1:
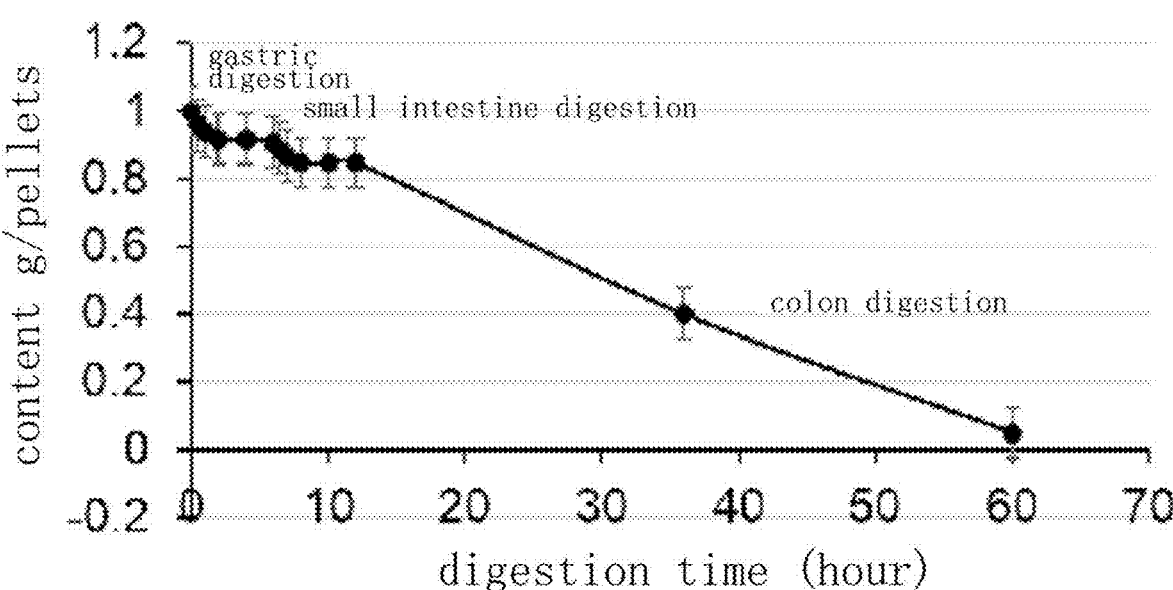
FIG. 1 is a schematic diagram illustrating a change of a content of xylitol in an enteral sustained-release sugar alcohol additive in a simulation digestion process of stomach, small intestine and colon according to the present disclosure.

In order to make the technical problems, technical solutions and beneficial effects of the present disclosure clearer, the present disclosure will be further described below in combination with the accompanying drawings and the specific embodiments. It should be understood that the specific embodiments described herein are merely used to explain the present disclosure rather than limit the present disclosure.

The present disclosure further provides a method of preparing an enteral sustained-release sugar alcohol additive, the enteral sustained-release sugar alcohol additive includes an inner layer structure and an outer layer structure, where the inner layer structure contains xylitol and agar, and the outer layer structure contains one of carrageenan or gellan gum or xanthan gum or guar gum, vitamin B12, L-arabinose, and fermented *Bifidobacterium* or fermented *Propionibacterium* or fermented *Lactobacillus*. In the enteral sustained-release sugar alcohol additive, a component ratio of the xylitol to the L-arabinose to the vitamin B12 is (1-33):1:0.005. The method includes the following steps: at step 1, mixing and sterilizing xylitol and agar, placing the mixture into a ball mould and standing the mixture for cooling so as to prepare xylitol agar pellets, a concentration of the agar being 2%; at step 2, preparing a carrageenan solution or gellan gum solution or xanthan gum solution or guar gum solution, adding the vitamin B12 and the L-arabinose to the carrageenan solution or the gellan gum solution or the xanthan gum solution or the guar gum solution and mixing to uniformity so as to obtain a mixed solution, and then wrapping the xylitol agar pellets in step 1 with the mixed solution to obtain xylitol agar two-layer colloidal pellets wrapped with the mixed solution; and at step 3, placing the two-layer colloidal pellets prepared in step 2 into a fermented *Bifidobacterium* medium or a fermented *Propionibacterium* medium or a fermented *Lactobacillus* medium for culturing, and then taking out the pellets for freeze drying or hot air drying to obtain the enteral sustained-release sugar alcohol additive.

In some embodiments, in the enteral sustained-release sugar alcohol additive, the component ratio of the xylitol to the L-arabinose to the vitamin B12 is (1-33):1:0.005.

In some embodiments, in the enteral sustained-release sugar alcohol additive, the component ratio of the xylitol to the L-arabinose to the vitamin B12 is (1-30):1:0.005. In some embodiments, in the enteral sustained-release sugar alcohol additive, the component ratio of the xylitol to the L-arabinose to the vitamin B12 is (1-28):1:0.005. In some embodiments, in the enteral sustained-release sugar alcohol additive, the component ratio of the xylitol to the L-arabinose to the vitamin B12 is (1-26):1:0.005. In some embodiments, in the enteral sustained-release sugar alcohol additive, the component ratio of the xylitol to the L-arabinose to the vitamin B12 is (1-24):1:0.005. In some embodiments, in the enteral sustained-release sugar alcohol additive, the component ratio of the xylitol to the L-arabinose to the vitamin B12 is (1-22):1:0.005. In some embodiments, in the enteral sustained-release sugar alcohol additive, the component ratio of the xylitol to the L-arabinose to the vitamin B12 is (1-20):1:0.005. In some embodiments, in the enteral sustained-release sugar alcohol additive, the component ratio of the xylitol to the L-arabinose to the vitamin B12 is (1-18):1:0.005. In some embodiments, in the enteral sustained-release sugar alcohol additive, the component ratio of the xylitol to the L-arabinose to the vitamin B12 is (1-16):1:0.005. In some embodiments, in the enteral sustained-release sugar alcohol additive, the component ratio of the xylitol to the L-arabinose to the vitamin B12 is (1-14):1:0.005. In some embodiments, in the enteral sustained-release sugar alcohol additive, the component ratio of the xylitol to the L-arabinose to the vitamin B12 is (1-12):1:0.005. In some embodiments, in the enteral sustained-release sugar alcohol additive, the component ratio of the xylitol to the L-arabinose to the vitamin B12 is (1-10):1:0.005. In some embodiments, in the enteral sustained-release sugar alcohol additive, the component ratio of the xylitol to the L-arabinose to the vitamin B12 is (1-8):1:0.005. In some embodiments, in the enteral sustained-release sugar alcohol additive, the component ratio of the xylitol to the L-arabinose to the vitamin B12 is (1-6):1:0.005. In some embodiments, in the enteral sustained-release sugar alcohol additive, the component ratio of the xylitol to the L-arabinose to the vitamin B12 is (1-4):1:0.005. In some embodiments, in the enteral sustained-release sugar alcohol additive, the component ratio of the xylitol to the L-arabinose to the vitamin B12 is (1-2):1:0.005. In some embodiments, in the enteral sustained-release sugar alcohol additive, the component ratio of the xylitol to the L-arabinose to the vitamin B12 may be 1:1:0.005, 2:1:0.005, 3:1:0.005, 4:1:0.005, 5:1:0.005, 6:1:0.005, 7:1:0.005, 8:1:0.005, 9:1:0.005. 10:1:0.005, 11:1:0.005, 12:1:0.005, 13:1:0.005, 14:1:0.005, 15:1:0.005, 16:1:0.005, 17:1:0.005, 18:1:0.005, 19:1:0.005, 20:1:0.005, 21:1:0.005, 22:1:0.005, 23:1:0.005, 24:1:0.005, 25:1:0.005, 26:1:0.005, 27:1:0.005, 28:1:0.005, 29:1:0.005, 30:1:0.005, 31:1:0.005, 32:1:0.005, 33:1:0.005, etc.

In some embodiments, the component ratio and the formulation ratio may be understood as a mass ratio, carrageenan, gellan gum, xanthan gum, or guar gum may be referred to as edible gum, and *Bifidobacterium, Propionibacterium* or *Lactobacillus* may be referred to as probiotics.

In the enteral sustained-release sugar alcohol additive of the present disclosure, by compounding xylitol, L-arabinose and vitamin B12, L-arabinose slows down metabolism of xylulose to arabitol and controls metabolic flux, vitamin B12 increases propionate metabolism pathways. In this way, increased gene expressions of Enterobacterium and Lachnospiraceae relating to xylitol are induced firstly, thereby increasing metabolism of xylitol to pentose phosphate pathway (PPP pathway), weakening the pathway in which xylu-lose is metabolized to arabitol and increasing propionate synthesis amount.

In the present disclosure, the enteral sustained-release sugar alcohol additive adopts two layers of structures. The two-layer colloid prepared using hydrocolloid such as car-rageenan and L-arabinose and vitamin B12 can realize sustained release of xylitol and L-arabinose in intestinal tract and their fixed-point release in colon.

The present disclosure further provides a method of preparing the enteral sustained-release sugar alcohol addi-tive as described above. The method includes the following steps.

At step 1, xylitol and agar are mixed and sterilized and then placed into a ball mould for standing cooling, so as to prepare xylitol agar pellets.

In some embodiments, a concentration of the agar is 2%.

In some embodiments, the mass ratio of the xylitol to the agar with a concentration of 2% may be in a range of 1:(1-5). For example, the mass ratio of the xylitol to the agar with a concentration of 2% may be 1:1, 1:2, 1:3, 1:4 or 1:5.

In some embodiments, in step 1, a sterilization condition may be sterilizing at 121° C. for 15 min-20 min (e.g., 15 min, 16 min, 17 min, 18 min, 20 min, etc.).

In some embodiments, the ball mould may be left to cool to 50° C.-55° C. For example, the ball mould may be left to cool to 50° C., 51° C., 52° C., 53° C., 54° C. or 55° C.

At step 2, a carrageenan solution or gellan gum solution or xanthan gum solution or guar gum solution is prepared, vitamin B12 and L-arabinose are added to the carrageenan solution or gellan gum solution or xanthan gum solution or guar gum solution and then mixed to uniformity so as to obtain a mixed solution, and then the xylitol agar pellets in step 1 are wrapped with the mixed solution to obtain xylitol agar two-layer colloidal pellets wrapped with the mixed solution.

In some embodiments, in step 2, a process of preparing the carrageenan solution or the gellan gum solution or the xanthan gum solution or the guar gum solution includes: weighing 2 g of the carrageenan or the gellan gum or the xanthan gum or the guar gum and dissolving in 100 ml of distilled water, sterilizing for 15 min-20 min at a temperature of 121° C. and cooling down to a temperature of 50° C.-60° C. (e.g., 50° C., 52° C., 55° C., 58° C., 60° C., etc.).

In some embodiments, the mass fraction of edible gum (e.g., carrageenan, gellan gum, xanthan gum, or guar gum) in the edible gum solution (e.g., the carrageenan solution, the gellan gum solution, the xanthan gum solution, or the guar gum solution) is 2%.

In some embodiments, the mass ratio of the L-arabinose to the vitamin B12 is 1:0.005.

In some embodiments, the mass ratio of the xylitol, the L-arabinose, and the vitamin B12 in the enteral sustained-release sugar alcohol additive may be in the range of (1-33):1:0.005.

In some embodiments, in step 2, preparing the carra-geenan solution, the gellan gum solution, the xanthan gum solution, or the guar gum solution may further include: adding the fermented *Bifidobacterium* medium or the fer-mented *Propionibacterium* medium or the fermented *Lac-tobacillus* medium to the carrageenan solution or the gellan gum solution or the xanthan gum solution or the guar gum solution. In step 2, the concentration of *Bifidobacterium* or *Propionibacterium* or *Lactobacillus* in the fermented *Bifi-dobacterium* medium or the fermented *Propionibacterium* medium or the fermented *Lactobacillus* medium may be 10⁹ CFU/mL. Adding the fermented *Bifidobacterium* medium or the fermented *Propionibacterium* medium or the fermented *Lactobacillus* medium to the carrageenan solution or the gellan gum solution or the xanthan gum solution or the guar gum solution can achieve the in-situ combination of probi-otics and edible gum, and improve the uniformity of the combination of probiotics and edible gum.

Since the edible gum solution prepared in step 2 includes the fermented probiotic medium, the two-layer colloidal pellets obtained in step 2 also include probiotics. Therefore, step 3 may omit the step of placing the two-layer colloidal pellets obtained in step 2 in the fermented probiotic medium for culturing, and directly perform freeze drying or hot air drying on the two-layer colloidal pellets obtained in step 2 to obtain the enteral sustained-release sugar alcohol addi-tive, which can simplify the process of preparing the enteral sustained-release sugar alcohol additive and improve its preparation efficiency.

At step 3, the two-layer colloidal pellets prepared in step 2 are placed into the fermented *Bifidobacterium* medium, or the fermented *Propionibacterium* medium or the fermented *Lactobacillus* medium for culturing, and then taken out for freeze drying or hot air drying to obtain the enteral sus-tained-release sugar alcohol additive.

In some embodiments, a ratio of the volume of the two-layer colloidal pellets prepared in step 2 to the volume of the fermented *Bifidobacterium* medium or the fermented *Propionibacterium* medium or the fermented *Lactobacillus* medium is 1:3.

In some embodiments, in step 3, the concentration of *Bifidobacterium* or *Propionibacterium* or *Lactobacillus* in the fermented *Bifidobacterium* medium or the fermented *Propionibacterium* medium or the fermented *Lactobacillus* medium may be 10⁹ CFU/mL.

In some embodiments, the two-layer colloidal pellets are placed in the fermented *Bifidobacterium* medium or the fermented *Propionibacterium* medium or the fermented *Lactobacillus* medium for culturing with 20 h-24 h (e.g., 20 h, 21 h, 22 h, 23 h or 24 h).

Freeze drying refers to removing water by sublimation at a low temperature to achieve the purpose of drying. In some embodiments, a time of freeze drying may be in a range of 1 h-24 h. In some embodiments, the time of freeze drying may be in a range of 5 h-20 h. In some embodiments, the time of freeze drying may be in a range of 10 h to 15 h. In some embodiments, the time of freeze drying may be 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, etc.

In some embodiments, a temperature of freeze drying may be in a range of −80° C.-(−50° C.). In some embodiments, the temperature of freeze drying may be in a range of −70° C.-(−60° C.).

Hot air drying refers to the evaporation of moisture by hot air to achieve the purpose of drying. In some embodiments, a time of the hot air drying may be 30 min-35 min (e.g., 30 min, 32 min, 34 min, or 35 min). In some embodiments, the temperature of hot air drying may be in a range of 50° C.-80° C. In some embodiments, the temperature of hot air drying can be in the range of 60° C.-70° C.

Different parameters of freeze drying or hot air drying may affect the survival rate of probiotics in the obtained enteral sustained-release sugar alcohol additive. For example, freeze drying refers to drying by removing water by sublimation at low temperature (e.g., below −50° C.), which can avoid damage to probiotics caused by liquid water phase change. If the temperature of freeze drying is high, it may cause damage to the probiotics, thereby reducing the survival rate of the probiotics. As another example, hot air drying refers to drying by evaporating water through hot air (e.g., in a range of 40° C.-80° C.). If the temperature of hot air is too high, the probiotic protein may be denatured and the membrane structure may be damaged, reducing the survival rate of the probiotics.

In some embodiments, in step 3, freeze drying may include: obtaining a size parameter of the ball mould in step 1; generating a plurality of candidate freezing parameters according to the size parameter; obtaining a first morphological image of the two-layer colloidal pellets in step 2, the concentration of *Bifidobacterium* or *Propionibacterium* or *Lactobacillus* in the fermented *Bifidobacterium* medium or fermented *Propionibacterium* medium or fermented *Lactobacillus* medium (which may be referred to as "probiotic concentration") in step 3, a culture time of the two-layer colloidal pellets placed in the fermented *Bifidobacterium* medium or the fermented *Propionibacterium* medium or the fermented *Lactobacillus* medium (which may be referred to as "culture time"), and a second morphological image of the two-layer colloidal pellets after culture; determining a target freezing parameter from the plurality of candidate freezing parameters based on the first morphological image, the probiotic concentration, the culture time, and the second morphological image; and performing freeze drying based on the target freezing parameter.

In some embodiments, the size parameter of the ball mould may include but is not limited to the radius. The size parameter of the ball mould may be obtained by measurement or from the product information of the ball mould.

In some embodiments, freeze drying may be freeze drying in stages. For example, freeze drying may include first stage freeze drying, second stage freeze drying, third stage freeze drying, etc. In some embodiments, each candidate freezing parameter may include a total freezing time, a count of freezing stages, and freezing parameters in each freezing stage. In some embodiments, the count of freezing stages refers to a count of freezing stages into which the entire freeze drying process is divided. In some embodiments, there may be at least two freezing stages. The total freezing time may be a sum of freezing times of the at least two freezing stages. The freezing time of each freezing stage may be the same or different. In some embodiments, the freezing parameters in each freezing stage may include but are not limited to the freezing time, the freezing temperature, etc., of the freezing stage.

According to different size parameters of different ball moulds, a plurality of candidate freezing parameters may be generated. Each candidate freezing parameter may correspond to a specific size parameter of the ball mould. In some embodiments, the candidate freezing parameters corresponding to the specific size parameter of the ball mould and the specific size parameter of the ball mould may be presented through a first preset table.

In some embodiments, the first preset table may be constructed by experiment. The first preset table may represent the correspondence between ball moulds with different size parameters and the candidate freezing parameters. In some embodiments, the size parameter of the ball mould may include but not limited to the radius. For example, the radius of the ball mould is r, and the candidate freezing parameter A (including the total freezing time, the count of freezing stages, the freezing time in each freezing stage, the freezing temperature and other parameters) is used to perform freeze drying on the two-layer colloidal pellets after culture in step 3 (obtained by processing the ball mould with a specific size parameter by performing the above steps 1 and 2 and probiotic culturing in step 3) to obtain a first candidate freezing result.

In some embodiments, the first candidate freezing result may include at least one of a residual moisture content, an abnormality rate, or a survival rate of probiotics (e.g., *Bifidobacterium* or *Propionibacterium* or *Lactobacillus*) of the two-layer colloidal pellets after freeze drying (obtained by processing the ball mould with a specific size parameter by performing the above steps 1 and 2 and probiotic culturing in step 3).

In some embodiments, the residual moisture content of the two-layer colloidal pellets after freeze drying may be determined by the Karl Fischer manner. In some embodiments, the abnormality rate may be understood as a ratio of an abnormal (e.g., deformed or cracked) area of the two-layer colloidal pellets after freeze drying to a total area, or a ratio of a length of cracks generated by the two-layer colloidal pellets after freeze drying to a diameter of the two-layer colloidal pellets after freeze drying. In some embodiments, the abnormality rate of the two-layer colloidal pellets after freeze drying may be obtained by measurement and calculation. In some embodiments, the count of probiotics in the two-layer colloidal pellets after freeze drying and the count of probiotics in the two-layer colloidal pellets after culture (which can be understood as the two-layer colloidal pellets before freeze drying) may be respectively measured by a plate counting manner, and a ratio of the two is used as the survival rate of the probiotics.

In some embodiments, the data recorded in the first preset table includes the size parameter and candidate freezing parameters of the ball mould corresponding to the first candidate freezing result that meets requirements. In some embodiments, the first candidate freezing result that meets requirements refers to a first candidate freezing result that meets at least one of the residual moisture content less than a preset residual moisture content, the abnormality rate less than a preset abnormality rate, or the survival rate of the probiotics greater than a preset survival rate. For different ball moulds (e.g., with different radii), a plurality of groups of experiments are performed using different candidate freezing parameters to obtain a plurality of first candidate freezing results. Further, the first candidate freezing results that meet the requirements are screened out, and the size parameter of the ball mould and the candidate freezing parameters corresponding to the first candidate freezing results that meet the requirements may be used as data in the first preset table. In some embodiments, the preset residual moisture content, the preset abnormality rate, and the preset survival rate of the probiotics may be determined by user customization.

In some embodiments, the first preset table may be queried according to the size parameter of the ball mould to obtain candidate freezing parameters corresponding to the specific size parameter of the ball mould.

In some embodiments, the first morphological image of the two-layer colloidal pellets in step 2 and the second morphological image of the two-layer colloidal pellets after culture in step 3 may be obtained by an imaging device (e.g., a camera, etc.). In some embodiments, the first morphological image may reflect the size parameter (e.g., the radius) of the two-layer colloidal pellets in step 2. In some embodiments, the second morphological image may reflect the size parameter (e.g., the radius) of the two-layer colloidal pellets after culture in step 3. In some embodiments, the probiotic concentration and culture time may be determined by statistical data.

In some embodiments, based on the first morphological image, the probiotic concentration, the culture time, and the second morphological image, determining the target freezing parameter from the plurality of candidate freezing parameters may include: querying a second preset table according to the first morphological image, the probiotic concentration, the culture time, and the second morphological image to obtain a plurality of second candidate freezing results corresponding to the first morphological image, the probiotic concentration, the culture time, and the second morphological image; determining an optimal second candidate freezing result from the plurality of second candidate freezing results; and querying the second preset table to obtain a candidate freezing parameter corresponding to the optimal second candidate freezing result as the target candidate freezing parameter.

In some embodiments, the second preset table may be constructed by experiment. The second preset table may represent the correspondence between the first morphological image, the probiotic concentration, the culture time, the second morphological image, the plurality of candidate freezing parameters and the plurality of candidate freezing results (which may be referred to as second candidate freezing results). In some embodiments, the plurality of candidate freezing parameters in the second preset table may be the same as the plurality of candidate freezing parameters in the first preset table, so as to improve the efficiency of constructing the second preset table and further improve the efficiency of determining the target freezing parameter.

In some embodiments, the second candidate freezing result may include at least one of the residual moisture content, the abnormality rate, or the survival rate of the probiotics of the two-layer colloidal pellets after freeze drying.

In some embodiments, the optimal second candidate freezing result refers to the minimum residual moisture content, the minimum abnormality rate or the maximum survival rate of the probiotics. In some embodiments, the optimal second candidate freezing result refers to an optimal (e.g., minimum) weighted value of the residual moisture content, the abnormality rate, and the survival rate of the probiotics. As an example, the second candidate freezing result W may be expressed as $W=aW_1+bW_2+cW_3$, where $W_1$ represents the residual moisture content, $W_2$ represents the abnormality rate, $W_3$ represents the survival rate of the probiotics, a and b are constants greater than 0, and c is a constant less than 0. The candidate freezing parameter corresponding to the second candidate freezing result with the minimum W may be determined as the target freezing parameter.

In some embodiments, determining the target freezing parameter from the plurality of candidate freezing parameters based on the first morphological image, the probiotic concentration, the culture time, and the second morphological image may include: for each of the candidate freezing parameters, inputting the first morphological image, the probiotic concentration, the culture time, the second morphological image, and the candidate freezing parameter into a determination model to obtain a candidate freezing result (which may be referred to as a third candidate freezing result) corresponding to the candidate freezing parameter; and determining the target freezing parameter based on the third candidate freezing results corresponding to the plurality of candidate freezing parameters.

In some embodiments, the third candidate freezing result may include the residual moisture content, the abnormality rate, and the survival rate of the probiotics of the two-layer colloidal pellets after freeze drying.

In some embodiments, the determination model may include a deep neural network model or a convolutional neural network model. In some embodiments, the determination model may be obtained by training an initial determination model with a plurality sets of experimental data. In some embodiments, during the training process of the determination model, the training sample may include a sample first morphological image, a sample probiotic concentration, a sample culture time, a sample second morphological image, and a sample candidate freezing parameter. The training label may include a sample third candidate freezing result corresponding to the sample first morphological image, the sample probiotic concentration, the sample culture time, the sample second morphological image, and the sample candidate freezing parameter.

In some embodiments, the training sample may be acquired based on experimental data. For example, a training sample may be obtained based on an experiment. For example, the data recorded in the experiment, such as the first morphological image, the second morphological image, the probiotic concentration, the culture time, and the actual freezing parameter, is used as the sample first morphological image, the sample second morphological image, the sample probiotic concentration, the sample culture time, and the sample candidate freezing parameter; the training label may include the sample residual water content (corresponding to a first sub-label), the sample abnormality rate (corresponding to a second sub-label), and the sample probiotic survival rate (corresponding to a third sub-label) of the two-layer colloidal pellets after freeze drying based on the sample candidate freezing parameter.

In some embodiments, the sample residual water content may be determined by the Karl Fischer manner to obtain the first sub-label. In some embodiments, if the two-layer colloidal pellets after freeze drying are not abnormal, the second sub-label takes a value of 0. If the two-layer colloidal pellets after freeze drying are abnormal, the second sub-label takes a value of 1. In some embodiments, the count of probiotics in the sample two-layer colloidal pellets before freeze drying and in the sample two-layer colloidal pellets after freeze drying may be measured by the plate counting manner, and the survival rate of the sample probiotics (a ratio of the count of probiotics in the sample two-layer colloidal pellets after freeze drying to the count of probiotics in the sample two-layer colloidal pellets before freeze drying) may be calculated as the third sub-label.

In some embodiments, the determination model may be obtained by training based on a plurality of labeled training samples. For example, the plurality of labeled training samples may be input into the initial determination model, and a loss function may be constructed by using the labels and the results of the initial determination model. The parameters of the initial determination model may be iteratively updated by gradient descent or other manners based on the loss function. When the preset conditions are met, the model training is completed and a trained determination model is obtained. The preset conditions may be the convergence of the loss function, the count of iterations reaching a threshold, etc.

In some embodiments, based on the third candidate freezing result corresponding to each candidate freezing parameter, determining the target freezing parameter may include: determining the candidate freezing parameter corresponding to the smallest residual moisture content, the smallest abnormality rate, or the largest survival rate of the probiotics in the third candidate freezing result as the target freezing parameter, or determining the candidate freezing parameter corresponding to the optimal (e.g., smallest) weighted value of the residual moisture content, the abnormality rate, and the survival rate of the probiotics in the third candidate freezing result as the target freezing parameter. For example, the third candidate freezing result V may be expressed as $xV_1 + yV_2 + zV_3$, wherein $V_1$ represents the residual moisture content, $V_2$ represents the abnormality rate, $V_3$ represents the survival rate of the probiotics, x and y are constants greater than 0, and z is a constant less than 0. The candidate freezing parameter corresponding to the third candidate freezing result with the smallest V may be determined as the target freezing parameter.

The method of preparing an enteral sustained-release sugar alcohol additive according to the present disclosure will be further described below in combination with specific embodiments.

Embodiment 1

According to a first embodiment of the present disclosure, the method of preparing an enteral sustained-release sugar alcohol additive may include the following steps.

At step 1, a given amount of xylitol was weighed and mixed with 2% agar, and then sterilized for 15 min at a temperature of 121° C.; when the mixture was cooled down to 55° C., the mixture was transferred to a ball mould by sucking using a disposable aseptic rubber head dropper and then stood and cooled down so as to prepare xylitol agar pellets.

At step 2, 2 g of carrageenan was weighed and dissolved in 100 ml of distilled water and then sterilized for 15 min at a temperature of 121° C. and then cooled down to 50° C.-60° C. with the temperature no greater than 60° C. to help vitamin B12 to stabilize and avoid light, and aseptic L-arabinose and vitamin B12 were added at a formulation ratio of 1:0.005 to the carrageenan solution and then mixed to uniformity; then the xylitol agar pellets were wrapped using the above mixed solution in an aseptic super-clean table to prepare two-layer colloidal pellets with a formulation ratio of xylitol, L-arabinose, and vitamin B12 as (1-33):1:0.005.

At step 3, the two-layer colloidal pellets prepared at step 2 were added to a *Bifidobacterium* fermentation ($10^9$ CFU/mL) broth at a ratio of 1:3 of total volume and stood for culture of 24 hours; then the pellets with bacteria were taken out and then subjected to freeze drying for 1 h-24 h or hot air drying for 30 min so as to obtain the enteral sustained-release sugar alcohol additive.

A new embodiment may be obtained by replacing *Bifidobacterium* with *Propionibacterium* or *Lactobacillus* in the above embodiment.

The enteral sustained-release sugar alcohol additive prepared in the embodiment is selected to perform simulation digestion experiment of stomach, small intestine and colon for verification in the following method.

1) Preparation of simulation gastric fluid: 0.62 g of NaCl, 0.22 g of KCl, 0.05 g of $CaCl_2$, and 0.12 g of $NaHCO_3$ were dissolved in 200 ml of distilled water, and adjusted to pH 2.0 using 0.1 M HCl solution to prepare a gastric fluid medium. Then, 1.0 mL of $CH_3COONa$ (1.0 mol/L, pH 5), 23.6 g of pepsase and 25.0 g of gastric lipase were added to 100 ml of the gastric medium and then the pH value of the gastric medium was adjusted to 2.0 using 0.1 M HCl solution.
2) Simulation of gastric fluid digestion: based on a dose of 1%-5% of a mass ratio of xylitol to the enteral sustained-release sugar alcohol additive pellets, the enteral sustained-release sugar alcohol additive pellets of the embodiment 1 were mixed with the simulation gastric fluid at a volume ratio of 1:1 and then subjected to water bath for 0.5 h, 1 h, 2 h, 4 h and 6 h at a temperature of 37° C. to respectively obtain digested samples.

3) Preparation of simulation small intestine digestive fluid: 0.54 g of NaCl, 0.065 g of KCl and 0.033 g of $CaCl_2$ were dissolved in 100 ml of distilled water and adjusted to pH 7.0 using 0.1 M NaOH solution to prepare a small intestine medium. Then, 6.5 mg of trypsin, 200.0 g of bile salt (4%, w/w) and 50.0 g of trypsin solution (7%, w/w) were added to the small intestine medium respectively, and then stirred continuously at room temperature using 0.1 M NaOH solution to adjust the solution pH to 7.5 so as to simulate a small intestine digestive fluid.

4) Simulation of small intestine digestion: the samples after simulation of gastric fluid digestion were mixed with the small intestine fluid respectively at a volume ratio of 3:7 and then subjected to water bath for 0.5 h, 1 h, 2 h, 4 h, and 6 h at a temperature of 37° C. so as to obtain digested samples respectively.

5) Based on a dose of 1%-5% of a mass ratio of xylitol to the two-layer colloidal pellets (without embedded *Bifidobacterium* cells) or the enteral sustained-release sugar alcohol additive pellets of embodiment 1, the two-layer colloidal pellet samples (without *Bifidobacterium* embedded) and the enteral sustained-release sugar alcohol additive pellets (with *Bifidobacterium* embedded) in the embodiment 1 were supplemented to CDMN (Chang Dao Mo Ni) colon in vitro simulation system to collect pellet samples simulating colon digestion of 24 h and 48 h.

Figure 2:
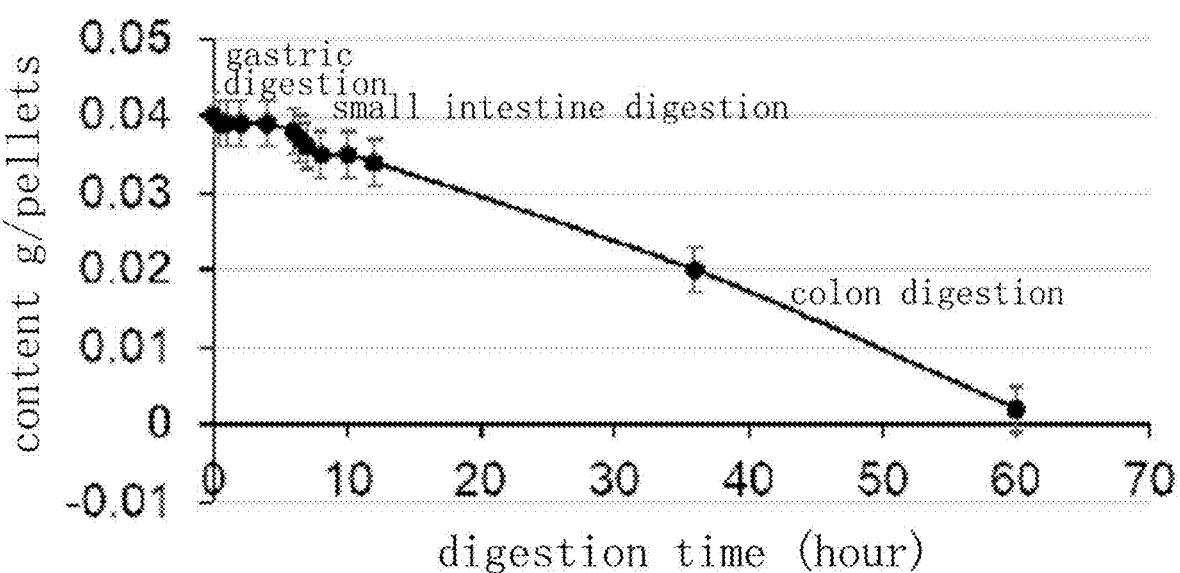
FIG. 2 is a schematic diagram illustrating a change of a content of L-arabinose in an enteral sustained-release sugar alcohol additive in a simulation digestion process of stomach, small intestine and colon according to the present disclosure.
Figure 3:
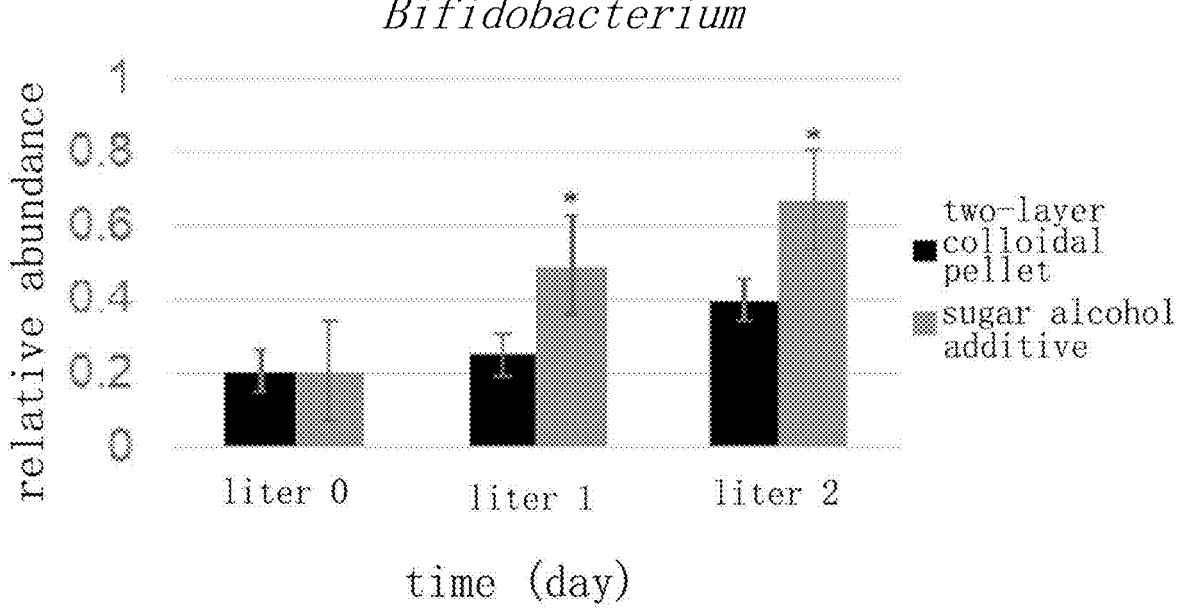
FIG. 3 is a comparative schematic diagram of relative abundances of *Bifidobacterium* of a two-layer colloidal pellet product and a finished enteral sustained-release sugar alcohol additive in a simulation colon experiment according to the present disclosure.

6) With HPLC, contents of xylitol and arabinose and an abundance value of *Bifidobacterium* retained in the pellets after simulation of gastric digestion, small intestine digestion and colon digestion were measured respectively to obtain comparison curves of FIGS. 1-3.

As shown in FIGS. 1 and 2, with a mass ratio of xylitol:L-arabinose being 25:1 as an example, in each pellet, the content of xylitol is 1 g, and the content of arabinose is 0.04 g. The first 6 hours relate to gastric digestion, the 6-12 hours relate to digestion of small intestine, and the 12-60 hours relate to contents of xylitol and arabinose retained in the pellets after microbial digestion of large intestine. Compared with the existing experimental data (the absorption rate of the small intestine for xylitol is 60% and the absorption rate for arabinose is 70%), the absorption rate of xylitol is only 15% and the absorption rate of arabinose is only 25% in the pellets of the present disclosure, and their cumulative release rates in the colon are about 95% respectively. It indicates that the enteral sustained-release sugar alcohol additive pellets of the present disclosure have the effect of slow and fixed-point release for xylitol and L-arabinose.

As shown in FIG. 3, compared with non-embedding (two-layer colloidal pellet product), the embedding of *Bifidobacterium* (the enteral sustained-release sugar alcohol additive) in the enteral sustained-release sugar alcohol additive pellets of the present disclosure can obviously promote the relative abundance of *Bifidobacterium* in the pellets, thereby promoting the relative abundance of *Bifidobacterium* in the colon.

As a result, the enteral sustained-release sugar alcohol additive of the present disclosure adopts layer-by-layer embedding technology to realize slow and layer-by-layer release of xylitol in intestinal tract and promote the relative abundance of *Bifidobacterium* in the colon.

The present disclosure further provides an application of the enteral sustained-release sugar alcohol additive as described above. The sugar alcohol additive is applied to foodstuff.

The present disclosure further provides an application of an enteral sustained-release sugar alcohol additive prepared using the method of preparing an enteral sustained-release sugar alcohol additive as described above. The sugar alcohol additive is applied to foodstuff.

For example, the enteral sustained-release sugar alcohol additive of the present disclosure is applied to beverage and cakes to promote generation of propionate in the colon of the human body and adjust intestinal health.

The above descriptions are merely made to preferred embodiments of the present disclosure and shall not be intended to limit the present disclosure. Any changes, equivalent substitutions and improvements and the like made within the spirit and principle of the present disclosure shall all fall within the scope of protection of the present disclosure.

What is claimed is:

1. A method of preparing an enteral sustained-release sugar alcohol additive, wherein:

the enteral sustained-release sugar alcohol additive includes an inner layer structure and an outer layer structure;

wherein the inner layer structure contains xylitol and agar;

wherein the outer layer structure contains:

(i) carrageenan, gellan gum, xanthan gum, or guar gum;

(ii) vitamin B12 and L-arabinose; and (iii) fermented *Bifidobacterium, Propionibacterium*, or *Lactobacillus;* wherein in the enteral sustained-release sugar alcohol additive, a component ratio of the xylitol to the L-arabinose to the vitamin B12 is (1-33):1:0.005;

wherein the method of preparing comprises the following steps:

1) mixing and sterilizing the xylitol and the agar, placing the mixture into a ball mould, and standing the mixture for cooling so as to prepare xylitol agar pellets, a concentration of the agar being 2%;

2) preparing a solution of carrageenan, gellan gum, xanthan gum, or guar gum, adding the vitamin B12 and the L-arabinose to the solution, and mixing to uniformity so as to obtain a mixed solution, and then wrapping the xylitol agar pellets prepared in step 1 with the mixed solution to obtain xylitol agar two-layer colloidal pellets wrapped with the mixed solution; and 3) placing the two-layer colloidal pellets prepared in step 2 into a fermentation medium containing *Bifidobacterium, Propionibacterium*, or *Lactobacillus* and culturing, and then taking out the two-layer colloidal pellets and freeze drying or hot air drying to obtain the enteral sustained-release sugar alcohol additive.

2. The method of claim 1, wherein in step 1, a sterilization condition is sterilizing for 15 min at a temperature of 121° C.

3. The method of claim 1, wherein in step 2, the solution of the carrageenan, the gellan gum, the xanthan gum, or the guar gum is prepared by weighing 2 g of the carrageenan, the gellan gum, the xanthan gum, or the guar gum, and dissolving in 100 ml of distilled water, sterilizing for 15 min at a temperature of 121° C. and cooling down to a temperature of 50° C.-60° C.

4. The method of claim 1, wherein in step 3, a concentration of *Bifidobacterium, Propionibacterium*, or *Lactobacillus* in the fermentation medium containing *Bifidobacterium, Propionibacterium*, or *Lactobacillus* is $10^9$ CFU/mL; and the two-layer colloidal pellets are placed in the fermentation medium containing *Bifidobacterium, Propionibacterium*, or *Lactobacillus* and cultured for 24 h, wherein a condition of freeze or hot air drying is freeze drying for 1 h-24 h or hot air drying for 30 min.

* * * * *